US010953185B2

United States Patent
Hlopick et al.

(10) Patent No.: US 10,953,185 B2
(45) Date of Patent: Mar. 23, 2021

(54) MOISTURE WICKING CONDUIT AND SYSTEM

(71) Applicant: KONINKLIJKE PHILIPS N.V., Eindhoven (NL)

(72) Inventors: Stephen George Hlopick, Murrysville, PA (US); Richard Thomas Haibach, Verona, PA (US)

(73) Assignee: Koninklijke Philips N.V., Eindhoven (NL)

( * ) Notice: Subject to any disclaimer, the term of this patent is extended or adjusted under 35 U.S.C. 154(b) by 414 days.

(21) Appl. No.: 15/935,405

(22) Filed: Mar. 26, 2018

(65) Prior Publication Data

US 2018/0280650 A1    Oct. 4, 2018

Related U.S. Application Data

(60) Provisional application No. 62/479,440, filed on Mar. 31, 2017.

(51) Int. Cl.
  *A61M 16/08*   (2006.01)
  *A61M 39/08*   (2006.01)
  *F16L 11/00*   (2006.01)

(52) U.S. Cl.
  CPC ........ *A61M 16/0808* (2013.01); *A61M 16/08* (2013.01); *A61M 16/0875* (2013.01);
  (Continued)

(58) Field of Classification Search
  CPC .......... A61M 16/0003; A61M 16/0057; A61M 16/06; A61M 16/0616; A61M 16/0622; A61M 16/0633; A61M 16/0638; A61M 16/0655; A61M 16/0808; A61M 16/0875; A61M 16/1055; A61M 16/106; A61M 16/1075; A61M 16/109; A61M 16/1095; A61M 16/142; A61M 16/16; A61M 16/161; A61M 16/162; A61M 2016/003; A61M 2205/0238; A61M 2205/3334; A61M 2205/3368; A61M 2206/14; B29C 2793/0045; B29C 48/0018; B29C 48/09; B29C 48/151; B29C 48/185; B29C 48/21;
  (Continued)

(56) References Cited

U.S. PATENT DOCUMENTS 1,566,512 A * 12/1925 Subers ................. B29D 23/001
                                                138/130
2,143,852 A *  1/1939 Anderson ............ B29D 23/001
                                                156/143
(Continued)

*Primary Examiner* — Annette Dixon
(74) *Attorney, Agent, or Firm* — Michael W. Haas

(57) ABSTRACT

A conduit for use in a pressure support system for communicating a flow of pressurized gas to the airway of a patient includes a first strip of a first material disposed helically about a central longitudinal axis such that subsequent helical convolutions of the first strip are disposed adjacent each other, and a second strip of a second material disposed helically about the central longitudinal axis along the first strip. The second strip is coupled between the subsequent helical convolutions of the first strip so as to form a hollow conduit. The first material is structured to prevent the passage of fluids therethrough. The second material is structured to allow passage of a liquid therethrough while inhibiting passage of gases therethrough.

15 Claims, 4 Drawing Sheets

(52) U.S. Cl.
CPC ........ *A61M 16/0883* (2014.02); *A61M 39/08* (2013.01); *F16L 11/00* (2013.01); *A61M 2205/7527* (2013.01)

(58) Field of Classification Search
CPC ....... B29C 53/08; B29C 53/58; B29C 53/581; B29D 23/001; B29K 2021/00; B29K 2105/06; B29K 2305/00; B29K 2995/0069; B29L 2009/003; B29L 2023/004; B29L 2023/005; B32B 1/08; B32B 27/00; B32B 3/18; B32B 37/16; B32B 7/02; D04C 1/02; D10B 2505/02; F16L 11/081; F16L 11/082; F16L 11/083; F16L 11/086; F16L 11/088; F16L 11/10; Y10S 138/08; Y10S 138/11; Y10T 428/13; Y10T 428/1393
See application file for complete search history.

(56) References Cited

U.S. PATENT DOCUMENTS

| | | | | |
|---|---|---|---|---|
| 4,106,968 | A | * | 8/1978 | Kutnyak ................. B29C 53/08 138/130 |
| 4,420,018 | A | * | 12/1983 | Brown, Jr. ............... D04C 1/02 138/124 |
| 8,028,692 | B2 | | 10/2011 | Ho |
| 8,714,204 | B2 | * | 5/2014 | Bryant ................. B29D 23/001 138/130 |
| 8,757,150 | B2 | * | 6/2014 | Davidowski ...... A61M 16/0808 128/204.17 |
| 9,067,397 | B2 | * | 6/2015 | Chen ..................... F16L 11/088 |
| 9,802,020 | B2 | | 10/2017 | Smith et al. |
| 2009/0025724 | A1 | | 1/2009 | Herron, Jr. |
| 2010/0083965 | A1 | * | 4/2010 | Virr ..................... A61M 16/109 128/203.26 |

* cited by examiner

MOISTURE WICKING CONDUIT AND SYSTEM

CROSS-REFERENCE TO RELATED APPLICATIONS

This patent application claims the priority benefit under 35 U.S.C. § 119(e) of U.S. Provisional Application No. 62/479,440 filed on Mar. 31, 2017, the contents of which are herein incorporated by reference.

BACKGROUND OF THE INVENTION

1. Field of the Invention

The present invention pertains to airway pressure support devices, and, in particular, to conduits for use in such systems which manages rainout.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory airflow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory airflow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

"Rainout" is a condition that occurs when the humidity of the air within the air flow path of a pressure support system (e.g. the CPAP unit, hose, and mask) condenses on the inside surfaces of the components of the air flow path, resulting in pooling of water within the airflow path over time (which is a nuisance to the patient receiving therapy). When rainout occurs, it often disturbs the patient, which in turn may cause the patient to discontinue therapy for the remainder of the night. Rainout occurs because the air within the airflow path is heated and humidified by a pressure support device or stand-alone humidifier (or the patient's own body in the case of exhaled air), but the temperatures of the walls of the airflow circuit (e.g. a hose or mask) are equilibrated with the ambient environment which may be significantly cooler than the air in the airflow circuit. The temperature of the air within the airflow circuit decreases when it makes contact with the walls of the circuit, resulting in condensation (i.e. "rainout"). Some pressure support systems attempt to reduce rainout by adding heating elements to the walls of the airflow circuit (e.g. a heated hose), but this is only a partial solution since it is impractical to add heating elements to all of the surfaces of the airflow circuit. Also, the addition of heating elements and associated electronics is expensive and adds additional weight to the system (especially important for wearable components). Another solution has been to add an insulating layer (e.g., a tube sock) to the outside of the components to try to reduce heat transfer through the walls of the components.

SUMMARY OF THE INVENTION

Accordingly, it is an object of the present invention to provide an arrangement for use in a pressure support system that overcomes the shortcomings of conventional arrangements. This object is achieved according to one embodiment of the present invention by providing a conduit for use in a pressure support system for communicating a flow of pressurized gas to the airway of a patient. The conduit comprises: a first strip of a first material having an outer surface and an opposite inner surface, the first strip disposed helically about a central longitudinal axis such that adjacent helical convolutions of the first strip overlap a predetermined distance in an overlapping region; and a second strip of a second material having an outer surface and an opposite inner surface, the second strip disposed helically about the central longitudinal axis along the first strip. The inner surface of the first strip in the overlapping region is coupled to the outer surface of the second strip and the outer surface of the first strip in the overlapping region is coupled to the inner surface of the second strip so as to form a tubular member. The first material is structured to prevent the passage of fluids therethrough. The second material is structured to allow passage of a liquid therethrough while inhibiting passage of gases therethrough.

The first material may comprise is a non-permeable material and the second material may comprise a hydrophilic material. The second material may be one of the group consisting of: nylon, polyester and spandex/elastene (e.g. LYCRA®). The conduit may further comprise a support member disposed in a helical manner about the central longitudinal axis along the outer surface of the first strip. The first strip may have a first width and the second strip may have a second width greater than the first width. The conduit may further comprise a support member disposed in a helical manner about the central longitudinal axis along the outer surface of the second strip.

This object is achieved according to another embodiment of the present invention by providing a conduit for use in a pressure support system for communicating a flow of pressurized gas to the airway of a patient. The conduit comprises: a first strip of a first material disposed helically about a central longitudinal axis such that subsequent helical convolutions of the first strip are disposed adjacent each other; and a second strip of a second material disposed helically about the central longitudinal axis along the first strip. The second strip is coupled between the subsequent helical convolutions of the first strip so as to form a hollow conduit therewith. The first material is structured to prevent the passage of fluids therethrough and the second material is structured to allow passage of a liquid therethrough while inhibiting passage of gases therethrough.

This object is achieved according to another embodiment of the present invention by providing a patient circuit for use in delivering a flow of a treatment gas to an airway of a patient. The patient circuit comprises: a patient interface device structured to engage about the airway of the patient and a conduit such as previously described.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
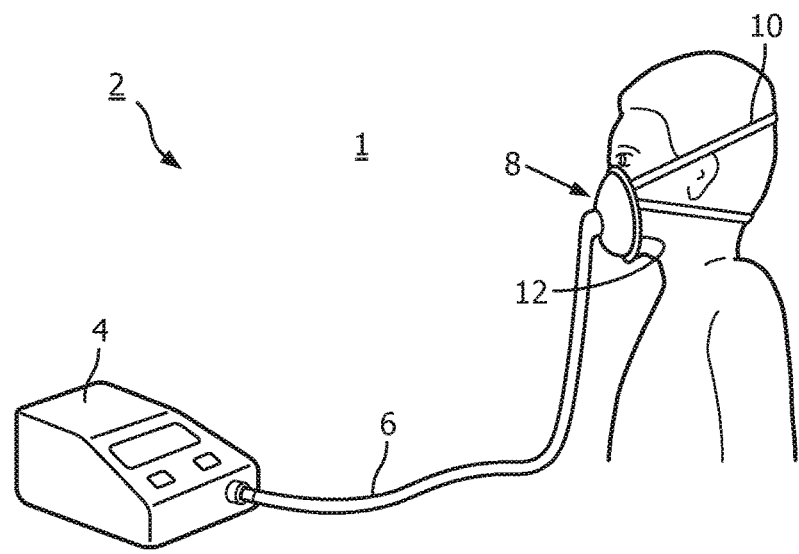
FIG. 1 is a simplified diagram of an airway pressure support system according to an exemplary embodiment, which is operated within an environment, such as a bedroom or home of the user of airway pressure support system, shown with a patient interface device thereof disposed on the face of a patient.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

As used herein, the term "dew point" shall mean the temperature at which the water vapor in a sample of air at constant barometric pressure condenses into liquid water at the same rate at which it evaporates. As used herein, a "fluid" refers to either a gas or a liquid (i.e., gases and liquids are both considered to be fluids).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present invention is directed generally to a system for removing liquid buildup in respiratory tubes as well as the conduit which performs the removal. The system employs a conduit comprising a hydrophilic material which draws liquid out of the interior of the tube conduit to the exterior of the conduit, where the liquid evaporates into the surrounding environment.

An example airway pressure support system 2 according to one particular, non-limiting exemplary embodiment of the present invention which is operated within an ambient environment 1, such as, without limitation, a bedroom or home of the user of airway pressure support system 2 is shown in FIG. 1. System 2 includes a pressure/flow generator 4, a delivery conduit 6, a patient interface device 8 structured to engage about an airway of the patient, and a headgear 10 for securing patient interface device 8 to the head of a patient (not numbered). Pressure generating device 4 is structured to generate a flow of breathing gas which may be heated and/or humidified. Pressure generating device 4 may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8. Delivery conduit 6 and patient interface device 8 are often collectively referred to as a patient circuit.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating device 4 is also referred to as a gas flow generating device, because flow results when a pressure gradient is generated. The present invention contemplates that pressure/flow generating device 4 is any conventional system for delivering a flow of gas to an airway of a patient or for elevating a pressure of gas at an airway of the patient, including the pressure support systems summarized above and non-invasive ventilation systems. Although described herein in example embodiments wherein a pressurized flow of gas is utilized, it is to be appreciated that embodiments of the invention as described herein could also be readily employed in other generally non-pressurized applications (e.g., without limitation, in high flow therapy applications).

In the exemplary embodiment, patient interface device 8 includes a patient sealing assembly 12, which in the illustrated embodiment is a full face mask. It is to be appreciated, however, that other types of patient sealing assemblies, such as, without limitation, a nasal/oral mask, a nasal cushion, or any other arrangements wherein rainout is a potential concern, which facilitate the delivery of the flow of breathing gas to the airway of a patient may be substituted for patient sealing assembly 12 while remaining within the scope of the present invention. It is also to be appreciated that headgear 10 is provided solely for exemplary purposes and that any suitable headgear arrangement may be employed without varying from the scope of the present invention.

Figure 2:
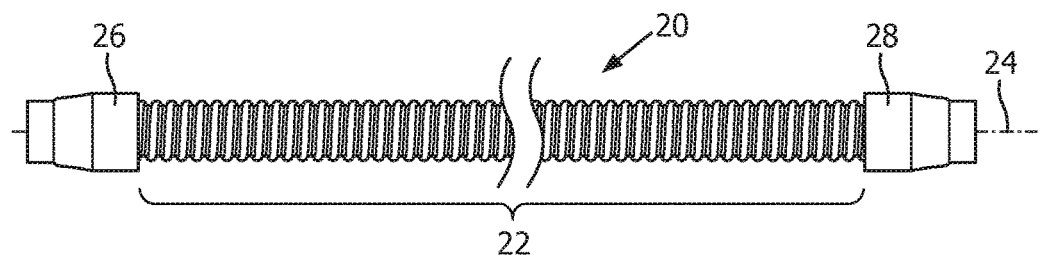
FIG. 2 is an elevation view of an example of a conventional delivery conduit which may be used in the system of FIG. 1.
Figure 3:
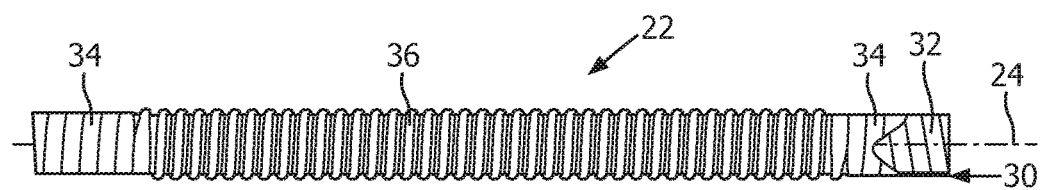
FIG. 3 is an elevation view of a portion of the conventional delivery conduit of FIG. 2 shown with portions removed to show internal details.
Figure 4:
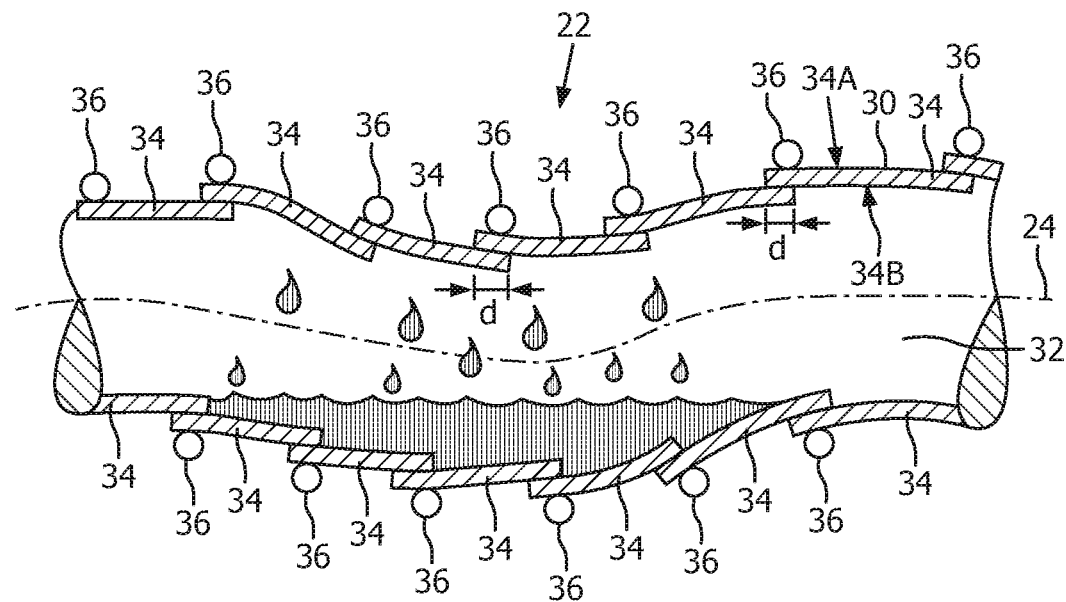
FIG. 4 is a partially schematic, sectional view of a portion of the conventional delivery conduit of FIG. 4 showing rainout and puddling resulting therefrom within the conduit.

An example of a conventional conduit 20 which is commonly used in system 2 is shown in FIGS. 2-4. Referring first to FIG. 2, conduit 20 generally includes a tubular body portion 22 which is disposed about a central longitudinal axis 24. Coupling members 26, 28 may be provided at respective ends of body portion 22 for use in coupling body portion 22 to pressure generating device 4 and patient interface device 8.

Referring now to FIGS. 3 and 4, body portion 22 generally includes a wall portion 30 which is of tubular shape and thus defines a passage 32 therein which is structured to communicated the flow of breathing gas from pressure generating device 4 to patient interface device 8. Wall portion 30 is generally formed from a thin, flexible strip 34 of material having an outer surface 34A and an opposite inner surface 34B which is disposed helically about central longitudinal axis 24 such that adjacent helical convolutions of strip 34 overlap a predetermined distance (d), and seal against each other (i.e., a portion of outer surface 34A of one convolute seals against inner surface 34B of the adjacent convolute), thus forming a continuous, generally flexible tube. In order to avoid undesirable crimping or crushing of such tube, body portion 22 further includes a support member 36 formed from a stiffer, more rigid material than strip 34. Support member 36 is disposed in a helical manner about central longitudinal axis 24 along outer surface 34A of strip 34. A drawback of such design is that water vapor (shown schematically as droplets w in FIG. 4) present in passage 32, which can condense on the inner surface 34B and puddle (such as shown schematically in FIG. 4), has nowhere to exit passage 32 aside from at the ends of conduit 20.

FIGS. 5-8 illustrate arrangements of conduits 40, 60 (in sectional views similar to that of FIG. 4) in accordance with example embodiments of the present invention which may be employed in place of conduit 6 in system 2 of FIG. 1. Conduits 40, 60 include mechanisms which reduce/eliminate liquid therefrom which may condense on the inner surfaces thereof.

Figure 5:
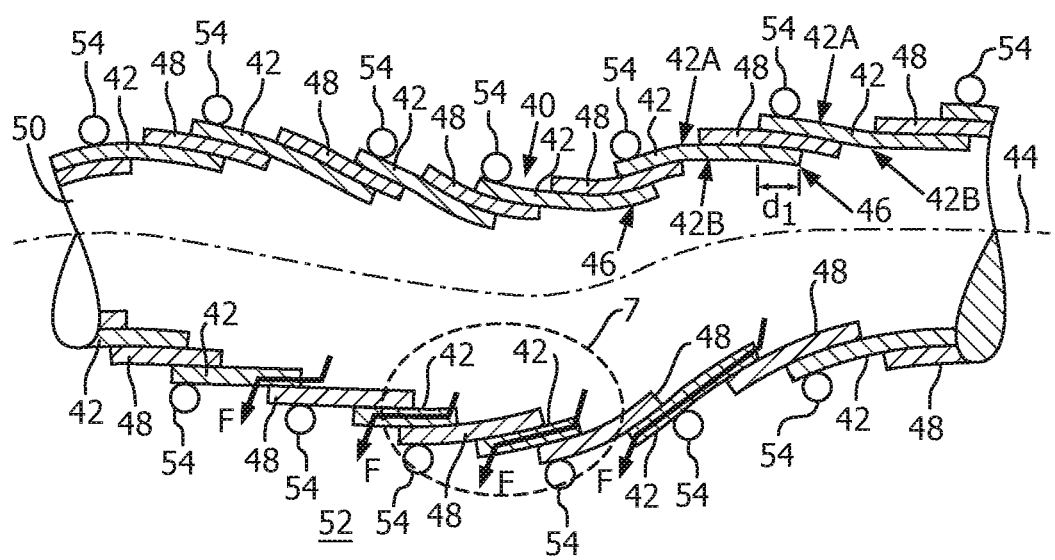
FIG. 5 is a partially schematic, sectional view of a portion of a conduit in accordance with an example embodiment of the present invention.
Figure 7:
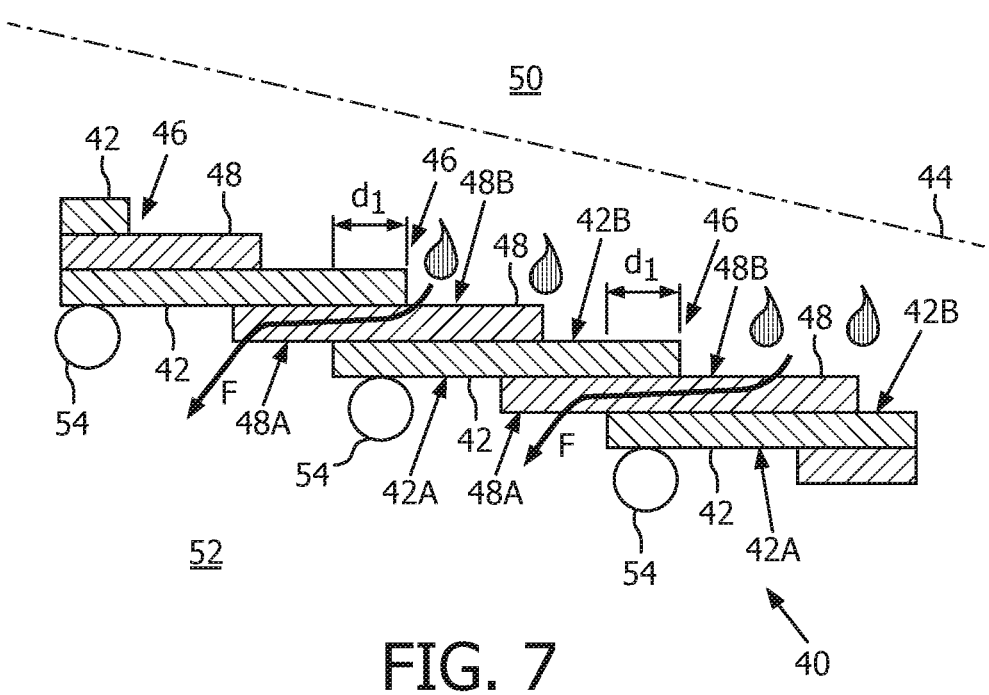
FIG. 7 is a partially schematic view of the portion of the sectional view of FIG. 5 as indicated at 7 in FIG. 5.

Referring first to FIGS. 5 and 7, conduit 40 is of generally similar construction as conduit 20 previously discussed and as such includes a first strip 42 formed of a first material having an outer surface 42A and an opposite inner surface 42B. In an example embodiment, first material is a non-permeable, flexible film (e.g., without limitation, polypropylene, polyethylene). First strip 42 is disposed helically about a central longitudinal axis 44 such that adjacent helical convolutions of first strip 42 overlap a predetermined distance $d_1$ in an overlapping region which is shown generally at 46.

Unlike conduit 20 in which adjacent convolutes of strip 34 directly engage/seal against each other, conduit 40 further includes a second strip 48 formed of a second material different from the first material of first strip 42. More particularly, second material is a hydrophilic material made from a wicking or hydrophilic fabric or film (e.g., without limitation, nylon, spandex/elastene (e.g., LYCRA®), polyester). Alternatively, second material could be a hydrophobic material with pores that promote a capillary reaction. Second strip 48 includes an outer surface 48A and an opposite inner surface 48B and is disposed helically about central longitudinal axis 44 along first strip 42. More particularly, second strip 48 is positioned relative to first strip 42 such that second strip 48 spans at least across the overlap distance $d_1$ and thus segregates inner surface 42B of first strip 42 from outer surface 42A of an adjacent convolute in overlapping region 46. Inner surface 42B of first strip 42 in overlapping region 46 is coupled to outer surface 48A of second strip 48 and outer surface 42A of first strip 42 in overlapping region 46 is coupled to inner surface 48B of second strip 48 so as to form a hollow conduit defining a passage therein 50 through which fluids may be communicated.

Unlike the conventional conduit 20 which traps liquids therein, the arrangement of conduit 40 provides a pathway (i.e., via second strip 48) along which any liquid (e.g., water) may exit passage 50 to the ambient environment 52. Arrows F in FIGS. 5 and 7 show an example of water exiting conduit 40 via such pathways. It is to be appreciated that due to positioning (i.e., spanning from passage 50 within conduit 40 to the exterior of conduit 40) and structure of the second material from which second strip 48 is formed, liquid is effectively wicked, via capillary action, from passage 50 to the outside of conduit 40 and to the ambient environment 52. Such pathways generally only allow liquid to pass therethrough, while inhibiting gas to pass therethrough (i.e., only allowing at most a negligible amount of gas to escape via such pathways). Hence, the exemplary arrangement shown in FIGS. 5 and 7 provides a solution for removing undesired liquid from the interior of a conduit used in providing a flow of breathing gas to a patient without appreciably affecting the flow of gas therethrough.

In order to avoid undesirable crimping or crushing of conduit 40, conduit 40 may further include a support member 54. Support member 54 may be formed from a generally rigid, or other suitable material. For example, rigid or semi-rigid thermoplastics like Hytrel®, polyethylene or polypropylene. Support member 54 could also include one or more wires inside for heating purposes, or could be composed primarily of a wire helix for crush resistance. Support member 54 is disposed in a helical manner about central longitudinal axis 44 along outer surface 42A of first strip 42.

Figure 6:
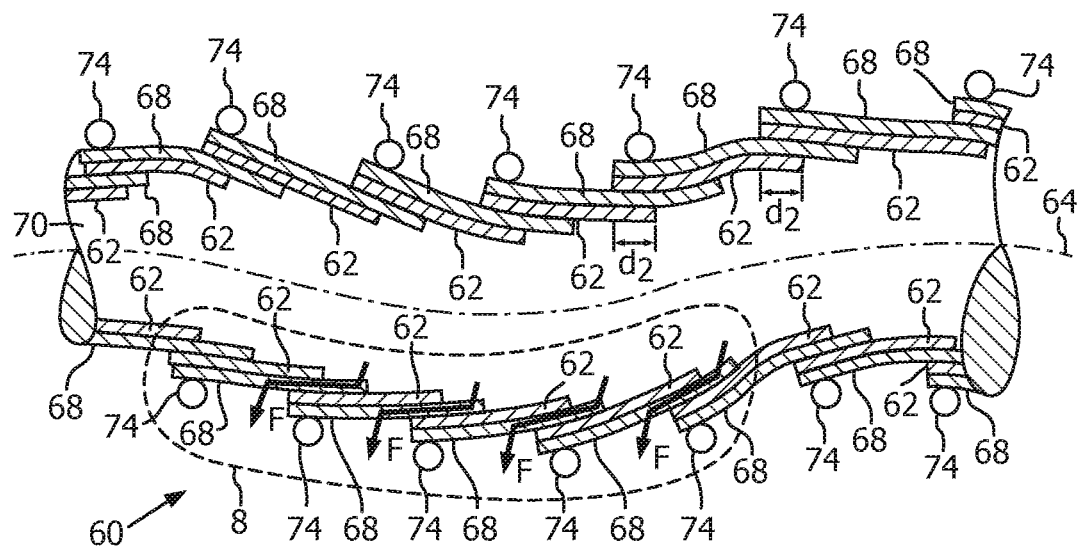
FIG. 6 is a partially schematic, sectional view of a portion of a conduit in accordance with another example embodiment of the present invention.
Figure 8:
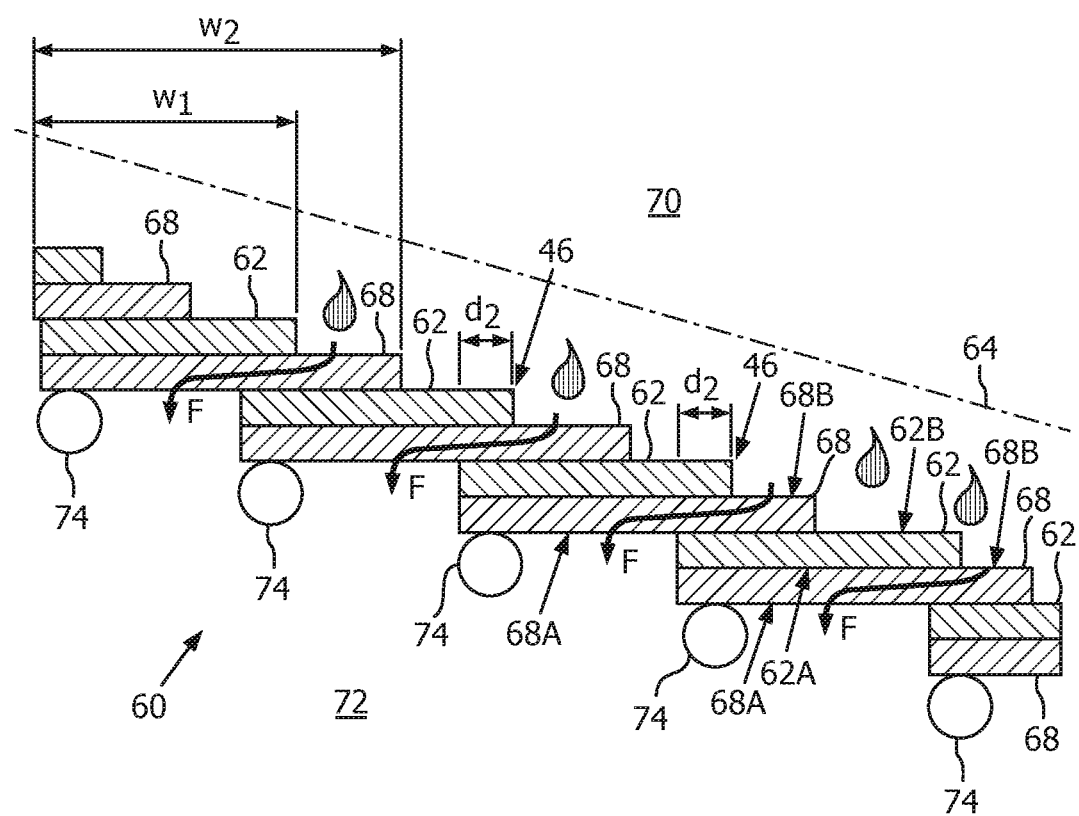
FIG. 8 is a partially schematic view of the portion of the sectional view of FIG. 6 as indicated at 8 in FIG. 6.

Referring now to FIGS. 6 and 8, conduit 60 is also of generally similar construction as conduits 20 and 40 previously discussed and as such includes a first strip 62 formed of a first material having an outer surface 62A, an opposite inner surface 62B, and a width $w_1$. In an example embodiment, first material is a non-permeable, flexible film (e.g., without limitation, polypropylene, polyethylene). First strip 42 is disposed helically about a central longitudinal axis 64 such that adjacent helical convolutions of first strip 62 overlap a predetermined distance $d_2$ in an overlapping region which is shown generally at 66.

Unlike conduit 20 in which adjacent convolutes of strip 34 directly engaged/sealed against each other, conduit 60, similar to conduit 40, further includes a second strip 68 formed of a second material different from the first material of first strip 62. More particularly, second material is a hydrophilic material made from a wicking or hydrophilic fabric or film (e.g., without limitation, nylon, spandex/elastene (e.g., LYCRA®), polyester). Alternatively, second material could be a hydrophobic material with pores that promote a capillary reaction. Second strip 68 includes an outer surface 68A, an opposite inner surface 68B, and width $w_2$ which is greater than width $w_1$ of first strip 62. Second strip 68 is disposed helically about central longitudinal axis 64 along first strip 62. More particularly, second strip 68 is positioned relative to first strip 62 such that second strip 68 spans across the entire width w of first strip 62, and thus spans across the entire width of the overlap distance $d_2$, thus segregating inner surface 62B of first strip 62 from outer surface 62A of an adjacent convolute in overlapping region 66. Inner surface 62B of first strip 62 in overlapping region 66 is coupled to outer surface 68A of second strip 48 and outer surface 62A of first strip 62 is coupled to inner surface 68B of second strip 68 so as to form a hollow conduit defining a passage therein 70 through which fluids may be communicated.

Unlike the conventional conduit 20 which traps liquids therein, the arrangement of conduit 60 provides a pathway (i.e., via second strip 68) along which any liquid (e.g., water) may exit passage 70 to the ambient environment 72. Arrows F in FIGS. 6 and 8 show an example of water exiting conduit 60 via such pathways. It is to be appreciated that due to positioning (i.e., spanning from passage 70 within conduit 60 to the exterior of conduit 60) and structure of the second material from which second strip 68 is formed, liquid is effectively wicked, via capillary action, from passage 70 to the outside of conduit 60 and to the ambient environment 72. Such pathways generally only allow liquid to pass therethrough, while only allowing at most a negligible amount of gas to escape via such pathways. Hence, the exemplary arrangement shown in FIGS. 6 and 8 provides a solution for removing undesired liquid from the interior of a conduit used in providing a flow of breathing gas to a patient without appreciably affecting the flow of gas therethrough. As the exterior of conduit 60 is generally covered by the second material of second strip 68, the exemplary conduit 60 shown in FIGS. 6 and 8 also provides for an arrangement which may be more comfortable upon contact with a patient.

In order to avoid undesirable crimping or crushing of conduit 60, conduit 60 may also include a support member 74 formed similarly or the same as support member 54 previously discussed. Support member 74 is disposed in a helical manner about central longitudinal axis 64 along outer surface 68A of second strip 68.

From the foregoing examples, it is to be appreciated that the positioning and structure of second materials provides for pathways along which liquid may be evacuated from the conduits. It is to be appreciated that in order to function, such materials must be in contact with both the interior of the conduit as well as the ambient environment. It is also to be appreciated, that it is not necessary for such pathways be continuous along the helix of first and second strips, but instead could instead be formed as distinct sections spanning across the second strip, thus providing discrete pathways.

Example embodiments of the present invention have been formed by extruding the first strip and support member while spinning around an axis and pulling in a direction parallel to that axis. The second strip is generally in the form of a "tape" which is fed along the first strip in the appropriate position relative thereto to form the desired final arrangement.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A conduit for use in a pressure support system for communicating a flow of pressurized gas to the airway of a patient, the conduit comprising:
   a first strip of a first material having an outer surface and an opposite inner surface, the first strip disposed helically about a central longitudinal axis such that adjacent helical convolutions of the first strip overlap a predetermined distance in an overlapping region; and
   a second strip of a second material having an outer surface and an opposite inner surface, the second strip disposed helically about the central longitudinal axis along the first strip,
   wherein the inner surface of the first strip in the overlapping region is coupled to the outer surface of the second strip and the outer surface of the first strip in the overlapping region is coupled to the inner surface of the second strip so as to form a tubular member,
   wherein the first material is structured to prevent the passage of fluids therethrough, and
   wherein the second material is structured to allow passage of a liquid therethrough while inhibiting passage of gases therethrough.

2. The conduit of claim 1, wherein the first material comprises a non-permeable material.

3. The conduit of claim 1, wherein the second material comprises a hydrophilic material.

4. The conduit of claim 1, wherein the second material is one of the group consisting of: nylon, polyester and spandex/elastene.

5. The conduit of claim 1, further comprising a support member disposed in a helical manner about the central longitudinal axis along the outer surface of the first strip.

6. The conduit of claim 1, wherein the first strip has a first width (w1) and wherein the second strip has a second width (w2) greater than the first width.

7. The conduit of claim 1, further comprising a support member disposed in a helical manner about the central longitudinal axis along the outer surface of the second strip.

8. A patient circuit for use in delivering a flow of a treatment gas to an airway of a patient, the patient circuit comprising:
   a patient interface device structured to engage about the airway of the patient; and
   a conduit for use in a pressure support system for communicating a flow of pressurized gas to the airway of a patient, the conduit comprising:
   a first strip of a first material having an outer surface and an opposite inner surface, the first strip disposed helically about a central longitudinal axis such that adjacent helical convolutions of the first strip overlap a predetermined distance in an overlapping region; and
   a second strip of a second material having an outer surface and an opposite inner surface, the second strip disposed helically about the central longitudinal axis along the first strip,
   wherein the inner surface of the first strip in the overlapping region is coupled to the outer surface of the second strip and the outer surface of the first strip in the overlapping region is coupled to the inner surface of the second strip so as to form a tubular member having an end coupled to the patient interface device,
   wherein the first material is structured to prevent the passage of fluids therethrough, and
   wherein the second material is structured to allow passage of a liquid therethrough while inhibiting passage of gases therethrough.

9. The patient circuit of claim 8, wherein the first material comprises a non-permeable material.

10. The patient circuit of claim 8, wherein the second material comprises a hydrophilic material.

11. The patient circuit of claim 8, wherein the second material is one of the group consisting of: nylon, polyester and spandex/elastene.

12. The patient circuit of claim 8, further comprising a support member disposed in a helical manner about the central longitudinal axis along the outer surface of the first strip.

13. The patient circuit of claim 8, wherein the first strip has a first width (w1) and wherein the second strip has a second width (w2) greater than the first width.

14. The patient circuit of claim 8, further comprising a support member disposed in a helical manner about the central longitudinal axis along the outer surface of the second strip.

15. A conduit for use in a pressure support system for communicating a flow of pressurized gas to the airway of a patient, the conduit comprising:
   a first strip of a first material disposed helically about a central longitudinal axis such that adjacent helical convolutions of the first strip overlap a predetermined distance; and
   a second strip of a second material disposed helically about the central longitudinal axis along the first strip,
   wherein the second strip is coupled between the adjacent helical convolutions of the first strip so as to form a hollow conduit therewith,
   wherein the first material is structured to prevent the passage of fluids therethrough, and
   wherein the second material is structured to allow passage of a liquid therethrough while inhibiting passage of gases therethrough.

* * * * *